United States Patent
Fryer et al.

(10) Patent No.: US 11,953,415 B2
(45) Date of Patent: Apr. 9, 2024

(54) METHOD AND A SYSTEM FOR DETERMINING ANALYTE CONTENT IN A FLUID IN A TREATMENT APPARATUS

(71) Applicant: ASP Global Manufacturing GmbH, Schaffhausen (CH)

(72) Inventors: Benjamin Fryer, Irvine, CA (US); Roger Vu, Irvine, CA (US); Joon Lee, Irvine, CA (US)

(73) Assignee: ASP Global Manufacturing GMBH (CH)

( * ) Notice: Subject to any disclaimer, the term of this patent is extended or adjusted under 35 U.S.C. 154(b) by 816 days.

(21) Appl. No.: 16/679,719

(22) Filed: Nov. 11, 2019

(65) Prior Publication Data

US 2020/0217772 A1 Jul. 9, 2020

Related U.S. Application Data (60) Provisional application No. 62/790,148, filed on Jan. 9, 2019.

(51) Int. Cl.
*G01N 15/06* (2006.01)
*A61B 1/00* (2006.01)
(Continued)

(52) U.S. Cl.
CPC ......... *G01N 15/06* (2013.01); *A61B 1/00057* (2013.01); *A61B 1/125* (2013.01); *C12Q 1/22* (2013.01); *G01N 2015/0693* (2013.01)

(58) Field of Classification Search
CPC ............ G01N 15/06; G01N 2015/0693; A61B 1/00057; A61B 1/125; C12Q 1/22
See application file for complete search history.

(56) References Cited

U.S. PATENT DOCUMENTS 5,032,186 A * 7/1991 Childers ................... A61L 2/07
422/26
5,140,842 A * 8/1992 Kiuchi .................... D06F 34/22
68/12.02
(Continued)

FOREIGN PATENT DOCUMENTS

EP 2198768 A1 6/2010
EP 3245939 A2 11/2017
(Continued)

OTHER PUBLICATIONS

WO-2018039443-A1 with English Machine Translation (Year: 2018).*
International Search Report and Written Opinion for PCT/IB2019/059665 dated Feb. 4, 2020.

*Primary Examiner* — Tri T Ton
*Assistant Examiner* — Jarreas Underwood
(74) *Attorney, Agent, or Firm* — Lerner David LLP (57) ABSTRACT

A method and a system for determining analyte content in a fluid in a treatment apparatus. The method comprises positioning a device for treatment in a treatment apparatus. A surface of the device is contacted with a fluid. An analyte content in the fluid is determined based on an electromagnetic property of the fluid following contacting the surface of the device with the fluid. More specifically, an electromagnetic property is measured. The measuring comprises emitting electromagnetic radiation into the fluid in the treatment apparatus and detecting electromagnetic radiation from the fluid. In another aspect, a system comprising a treatment apparatus and a detector for determining the analyte content in the fluid in the treatment apparatus is provided.

25 Claims, 4 Drawing Sheets

(51) Int. Cl.
 *A61B 1/12* (2006.01)
 *C12Q 1/22* (2006.01)

(56) References Cited

U.S. PATENT DOCUMENTS

| | | | | |
|---|---|---|---|---|
| 5,220,179 | A * | 6/1993 | Gagea | G01V 8/10 |
| | | | | 250/214 RC |
| 5,259,219 | A * | 11/1993 | Dausch | D06F 34/22 |
| | | | | 137/561 A |
| 5,291,626 | A * | 3/1994 | Molnar | A47L 15/4297 |
| | | | | 68/12.02 |
| 5,396,178 | A * | 3/1995 | Rybarski | G01N 27/021 |
| | | | | 210/85 |
| 5,500,050 | A * | 3/1996 | Chan | A47L 15/0055 |
| | | | | 137/897 |
| 5,872,359 | A * | 2/1999 | Stewart | A61L 2/24 |
| | | | | 250/339.09 |
| 6,435,424 | B1 * | 8/2002 | Pauley | G05D 23/1951 |
| | | | | 239/128 |
| 7,246,627 | B2 * | 7/2007 | Jacobs | A61B 90/70 |
| | | | | 134/113 |
| 7,431,886 | B2 * | 10/2008 | Centanni | G01N 33/0032 |
| | | | | 422/82.01 |
| 10,702,619 | B2 * | 7/2020 | Fang | G01N 31/226 |
| 2001/0033805 | A1 * | 10/2001 | Jacobs | A61B 90/70 |
| | | | | 422/62 |
| 2004/0163679 | A1 * | 8/2004 | Jung | A47L 15/4297 |
| | | | | 134/25.2 |
| 2011/0076189 | A1 * | 3/2011 | McVey | A61L 2/24 |
| | | | | 422/105 |
| 2016/0175051 | A1 * | 6/2016 | Matta | C11D 7/263 |
| | | | | 510/161 |
| 2020/0237203 | A1 * | 7/2020 | Zilligen | A61B 1/00137 |
| 2021/0386894 | A1 * | 12/2021 | Bracher | A61L 2/24 |

FOREIGN PATENT DOCUMENTS

| | | |
|---|---|---|
| WO | WO 97/04816 A1 | 2/1997 |
| WO | WO 2018/039443 A1 | 3/2018 |

* cited by examiner

000# METHOD AND A SYSTEM FOR DETERMINING ANALYTE CONTENT IN A FLUID IN A TREATMENT APPARATUS

CROSS REFERENCE TO RELATED APPLICATIONS

The present application claims priority under 35 U.S.C. § 120 to co-pending U.S. provisional Patent Application Ser. No. 62/790,148, filed Jan. 9, 2019, which is incorporated by reference herein in its entirety.

FIELD

The present disclosure relates to a method and a system for determining analyte content in a fluid in a treatment apparatus.

BACKGROUND

Medical devices are used in numerous procedures in the medical field. These devices are as varied as the procedures themselves. As such, proper care of these devices can be critical for efficient, effective, and safe use of the devices during treatment of the patient.

After a medical device is used, the medical device can be cleaned, disinfected, and/or sterilized in order to prepare the medical device for its next use. This treatment process may include placing the medical device in a re-processing machine, such as an endoscope re-processor, and contacting the medical device with a fluid that cleans, disinfects, and/or sterilizes the device.

Improving health and safety conditions for patients, as well as improving patient treatment processes are an important focus of the medical field. In this regard, efforts have been made to improve the efficiency and effectiveness of cleaning, disinfecting, and/or sterilizing processes for medical devices.

SUMMARY

The present disclosure provides a method comprising positioning a device for treatment in a treatment apparatus. The method comprises contacting a surface of the device with a fluid. An analyte content in the fluid is determined based on an electromagnetic property of the fluid following contacting the surface of the device with the fluid. An electromagnetic property of the fluid is measured, comprising emitting electromagnetic radiation into the fluid in the treatment apparatus, and detecting electromagnetic radiation from the fluid.

The present disclosure also provides a system comprising a treatment apparatus and a detector for determining the analyte content in the fluid in the treatment apparatus. The detector is configured for electromagnetic communication with the treatment apparatus. The detector comprises an electromagnetic radiation source configured to emit electromagnetic radiation into the fluid in the treatment apparatus and an electromagnetic radiation sensor suitable to detect electromagnetic radiation from the fluid. The detector is configured to measure an electromagnetic property of the fluid based on detected electromagnetic radiation from the fluid to determine the analyte content in the fluid.

The present disclosure also provides a system comprising an endoscope re-processor comprising a pathway in fluid communication with a surface of an endoscope, the surface of the endoscope comprising protein. The endoscope re-processor comprises a detector for determining the protein content in the fluid in the endoscope re-processor and the detector is configured for electromagnetic communication with the endoscope re-processor. The detector comprises an electromagnetic radiation source configured to emit electromagnetic radiation at a wavelength in a range of 190 nm to 700 nm into the fluid in the endoscope re-processor. The detector comprises an electromagnetic radiation sensor configured to detect electromagnetic radiation at a wavelength in a range of 190 nm to 700 nm from the fluid. The detector is configured to measure an electromagnetic property of the fluid based on the detecting to determine the protein content in the fluid.

It is understood that the inventions described in this specification are not limited to the examples summarized in this Summary. Various other aspects are described and exemplified herein.

BRIEF DESCRIPTION OF THE DRAWINGS

The features and advantages of the examples, and the manner of attaining them, will become more apparent and the examples will be better understood by reference to the following description of examples taken in conjunction with the accompanying drawings, wherein.

Corresponding reference characters indicate corresponding parts throughout the several views. The exemplifications set out herein illustrate certain examples, in one form, and such exemplifications are not to be construed as limiting the scope of the examples in any manner.

DETAILED DESCRIPTION

Certain exemplary aspects of the present disclosure will now be described to provide an overall understanding of the principles of the structure, function, manufacture, and use of the devices and methods disclosed herein. One or more examples of these aspects are illustrated in the accompanying drawings. Those of ordinary skill in the art will understand that the devices and methods specifically described herein and illustrated in the accompanying drawings are non-limiting exemplary aspects and that the scope of the various examples of the present disclosure is defined solely by the claims. The features illustrated or described in connection with one exemplary aspect may be combined with the features of other aspects. Such modifications and variations are intended to be included within the scope of the present disclosure.

Any patent, publication, or other disclosure material identified herein is incorporated by reference into this specification in its entirety unless otherwise indicated, but only to the extent that the incorporated material does not conflict with existing descriptions, definitions, statements, or other disclosure material expressly set forth in this specification.

As such, and to the extent necessary, the express disclosure as set forth in this specification supersedes any conflicting material incorporated by reference. Any material, or portion thereof, that is said to be incorporated by reference into this specification, but which conflicts with existing definitions, statements, or other disclosure material set forth herein, is only incorporated to the extent that no conflict arises between that incorporated material and the existing disclosure material. Applicants reserve the right to amend this specification to expressly recite any subject matter, or portion thereof, incorporated by reference herein.

Any references herein to "various examples," "some examples," "one example," "an example," similar references to "aspects," or the like, means that a particular feature, structure, or characteristic described in connection with the example is included in at least one example. Thus, appearances of the phrases "in various examples," "in some examples," "in one example," "in an example," similar references to "aspects," or the like, in places throughout the specification are not necessarily all referring to the same example. Furthermore, the particular features, structures, or characteristics may be combined in any suitable manner in one or more examples. Thus, the particular features, structures, or characteristics illustrated or described in connection with one example may be combined, in whole or in part, with the features, structures, or characteristics of one or more other examples without limitation. Such modifications and variations are intended to be included within the scope of the present examples.

In this specification, unless otherwise indicated, all numerical parameters are to be understood as being prefaced and modified in all instances by the term "about", in which the numerical parameters possess the inherent variability characteristic of the underlying measurement techniques used to determine the numerical value of the parameter. At the very least, and not as an attempt to limit the application of the doctrine of equivalents to the scope of the claims, each numerical parameter described herein should at least be construed in light of the number of reported significant digits and by applying ordinary rounding techniques.

Also, any numerical range recited herein includes all sub-ranges subsumed within the recited range. For example, a range of "1 to 10" includes all sub-ranges between (and including) the recited minimum value of 1 and the recited maximum value of 10, that is, having a minimum value equal to or greater than 1 and a maximum value equal to or less than 10. Any maximum numerical limitation recited in this specification is intended to include all lower numerical limitations subsumed therein and any minimum numerical limitation recited in this specification is intended to include all higher numerical limitations subsumed therein. Accordingly, Applicant reserves the right to amend this specification, including the claims, to expressly recite any sub-range subsumed within the ranges expressly recited.

The grammatical articles "a," "an," and "the," as used herein, are intended to include "at least one" or "one or more," unless otherwise indicated, even if "at least one" or "one or more" is expressly used in certain instances. Thus, the articles are used herein to refer to one or more than one (i.e., to "at least one") of the grammatical objects of the article. Further, the use of a singular noun includes the plural, and the use of a plural noun includes the singular, unless the context of the usage requires otherwise.

A device can undergo a treatment process to prevent cross-contamination and the spread of disease. As used herein, a "treatment process" may be a cleaning process, a disinfecting process, a sterilization process, the like, and combinations thereof. A treatment process may be either manual, automated, or some combination thereof, and may utilize a treatment agent. As used herein, a "treatment agent" can comprise at least one of a cleaning agent, a disinfectant, and a sterilant. As used herein a "cleaning process" means a treatment process employing a cleaning agent that removes and/or eliminates debris such as, for example, a dirt, a dust, a particle, an oil, a protein, a carbohydrate, and the like. As used herein, a "cleaning agent" means a type of treatment agent that removes and/or eliminates debris during a cleaning process such as, for example, a surfactant and/or a detergent.

A disinfecting process and a sterilization process can remove and/or eliminate a bioburden from a device. A bioburden may be, for example, a bacterium (e.g., mycobacterium, bacterial spores), an archaeon, a eukaryote, a virus, a fungus, and/or other forms of biological agents. Bacterial spores (e.g., endospores) are a form of bacteria which are dormant and highly resistive to physical and chemical degradation. As used herein, a "disinfecting process" means a treatment process that substantially removes a bioburden except for bacterial spores. As used herein, "substantially remove" means that at least 99% of the bioburden has been removed from the device such as, for example, at least 99.9% of the bioburden, at least 99.99% of the bioburden, at least 99.999% of the bioburden, or at least 99.9999% of the bioburden has been removed from the device. As used herein, a "sterilization process" means a treatment process which substantially removes a bioburden including bacterial spores. The sterilization process may include, for example, the addition of heat, freezing, a sterilant, irradiation, pressure, and combinations thereof. The sterilant may comprise a chemical capable of sterilization. The disinfection process may include, for example, the addition of heat, a disinfectant, irradiation, pressure, and combinations thereof. The disinfectant may comprise a chemical capable of disinfection.

A treatment process for a device, such as, for example, a medical device, can comprise various processing steps. For example, the treatment process can comprise bulk removal and/or elimination of debris from the device (e.g., cleaning) and removal and/or elimination of bioburden (e.g., disinfection, sterilization) from the device. Each device can have varying amounts of debris and/or bioburden which can affect the treatment process. For example, use of a medical device on a patient can result in a device which can be soiled to various levels, depending on the medical procedure(s) that are performed. Manufacturing the medical device can also soil the device to various levels. Measuring the level of debris and/or bioburden on the device can enable adjustment of the treatment process and can ensure that a treatment process can remove and/or eliminate debris and/or bioburden from the device. Thus, provided herein is a method and a system for determining an analyte content in a fluid within a treatment apparatus to aid in the treatment process.

Figure 1:
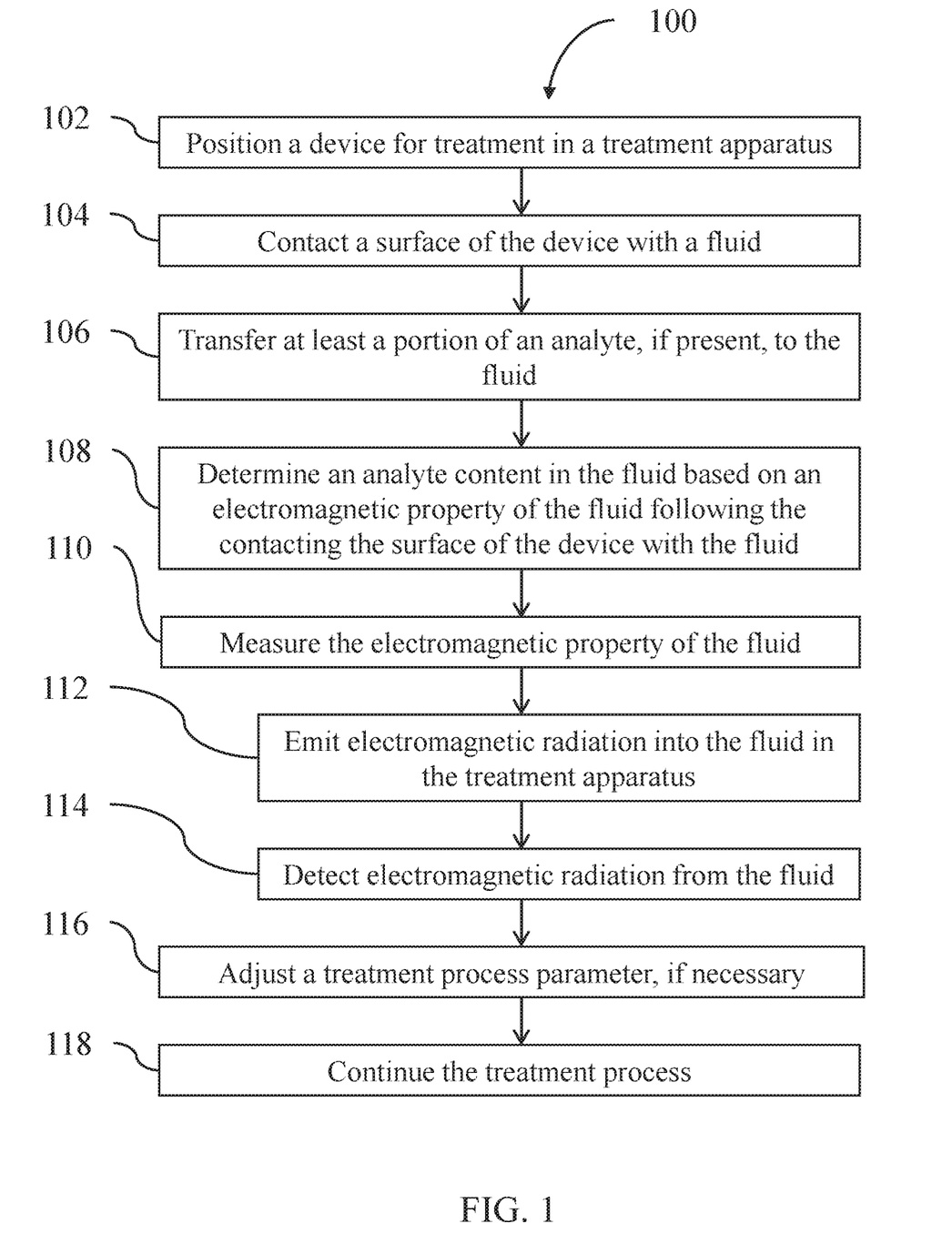
FIG. 1 is a flow chart illustrating a non-limiting example of a method for determining an analyte content in a fluid in a treatment apparatus according to the present disclosure.

Referring to FIG. 1, a flow chart 100 is provided that illustrates a non-limiting example of a method for determining an analyte content in a fluid according to the present disclosure. In particular, provided herein is a method for determining an analyte content in a fluid, comprising positioning a device for treatment in the treatment apparatus, 102. For example, the device can be a re-processing apparatus, such as an endoscope re-processor. The device can be positioned in a basin of the treatment apparatus and covered with a lid. The device can be configured in fluid communication with the treatment apparatus via a fluid connection (e.g., a tube, a fitting). For example, a lumen of the device can be configured in fluid communication with the treatment apparatus via a fluid connection.

A surface of the device can be contacted with a fluid, 104. Contacting the surface of the device can be by various means and can comprise, for example, at least one of spraying the device with the fluid, submerging the device in the fluid, and flowing the fluid over the surface of the device (e.g., via a fluid connection). The device can comprise a medical device, such as, for example, at least one of an endoscope, forceps, a clamp, a retractor, a cutter, a dilator, a tube, a fitting, a stapler, a needle, a drill, a scope, and a probe. The surface of the device can comprise at least one of an outer surface and an inner surface (e.g., luminal surface).

The fluid can be any suitable fluid, such as one for cleaning, disinfecting, and/or sterilizing the surface and can comprise, for example, at least one of water, a treatment agent, a surfactant, analyte, a reagent, a reagent-analyte complex, and a chemical species formed via chemical interaction between the reagent and the analyte. The fluid can comprise water, surfactant, and analyte. The fluid can comprise water. The fluid can comprise water and analyte. The fluid can comprise water and a chemical species formed via chemical interaction between the reagent and the analyte. The treatment agent can comprise a cleaning agent suitable for dissolving and/or suspending the analyte, such as, for example, a surfactant. For example, the surfactant can comprise 4-(1,1,3,3-tetramethylbutyl)phenyl-polyethylene glycol and/or polyoxyethylene(20)sorbitan monolaurate. The surfactant can be TWEEN® 20 (CAS No. 9005-64-5) which comprises 4-(1,1,3,3-tetramethylbutyl)phenyl-polyethylene glycol and is available from Sigma Aldrich, Saint Louis, Missouri. The surfactant can be Triton™ X-100 (CAS No. 9002-93-1) which comprises polyoxyethylene(20)sorbitan monolaurate and is available from Sigma Aldrich, Saint Louis, Missouri. The surfactant can comprise an electromagnetic property such that the surfactant may cause minimal, if any, interference with the measurement of an electromagnetic property of the fluid.

The fluid can comprise at least 0.01% surfactant by weight based on the total weight of the fluid, such as, for example, at least 0.1% surfactant by weight, at least 0.5% surfactant by weight, at least 1.0% surfactant by weight, at least 1.5% surfactant by weight, or at least 2% surfactant by weight, based on the total weight of the fluid. The fluid can comprise 5% or less surfactant by weight based on the total weight of the fluid, such as, for example, 2% or less surfactant by weight, 1.5% or less surfactant by weight, 1.0% or less surfactant by weight, 0.5% or less surfactant by weight, or 0.1% or less surfactant by weight based on the total weight of the fluid. The fluid can comprise 0.01% to 5% surfactant by weight based on the total weight of the fluid, such as, for example, 0.1% to 2% surfactant by weight or 0.5% to 2% surfactant by weight, based on the total weight of the fluid.

The surface of the device can comprise analyte. For example, the device may have been previously used in a medical procedure, and analyte may have accumulated on the device. The analyte can comprise at least one of a protein, a carbohydrate, a lipid, a peptide, a nucleic acid, a polynucleotide, a bacterium, a virus, a spore (e.g., a bacterial endospore), a eukaryote, an archaeon, a treatment agent, and a contaminate from a manufacturing and/or packaging process. Evaluating the amount of analyte on a surface of a device can aid in performance of a treatment process of the device. For example, a device comprising a higher amount of analyte can be more difficult to clean, disinfect, and/or sterilize than a device comprising a lower amount of analyte, and require, for example, a longer processing time, more concentrated or harsher treatment fluids, or a different combination of process conditions. For example, a device comprising a higher amount of analyte can comprise a higher amount of bioburden. The higher amount of bioburden can reduce the effect of cleaning agent, disinfectant, and/or sterilant due to interference therewith by the analyte.

Referring again to FIG. 1, the method of the present disclosure can further comprise transferring at least a portion of analyte, if present, from the device to the fluid, 106. For example, analyte can be dissolved and/or suspended into the fluid. The dissolving and/or suspending can be facilitated by, for example, at least one of mechanically brushing and/or scrubbing the surface, submerging the device in the fluid, flowing the fluid over a surface of the device, spraying the fluid onto a surface of the device, and vibrating the fluid and/or the device. By transferring at least a portion of analyte, if present, from the device to the fluid, the amount of analyte on a surface of a device can be evaluated.

The method of the present disclosure can further comprise determining the analyte content in the fluid (e.g., dissolved and/or suspended analyte within the fluid) based on an electromagnetic property of the fluid following contacting the surface of the device with the fluid, 108. For example, the analyte content, such as an analyte concentration, a particle size, and/or a particle distribution within the fluid can be determined. The analyte concentration can be a molar concentration, a mass per unit volume concentration, a volume per unit volume concentration, a mass per unit area concentration, variations thereof, and combinations thereof. In order to determine the analyte content, the method of the present disclosure can comprise measuring the electromagnetic property of the fluid, 110. The electromagnetic property of the fluid can comprise at least one of absorbance, transmittance, scattering, photoluminescence, and reflectance. The composition of the fluid can affect the electromagnetic property of the fluid. For example, an analyte content, a water content, a treatment agent content, and a reagent content can affect the electromagnetic property of the fluid.

In order to measure the electromagnetic property, the method of the present disclosure may comprise emitting electromagnetic radiation into the fluid in the treatment apparatus, 112. The emitted electromagnetic radiation can pass through the fluid, and the fluid may change or may not change the emitted electromagnetic radiation. For example, an electromagnetic property of the fluid may change the emitted electromagnetic radiation (e.g., absorb, scatter), or the fluid can emit secondary electromagnetic radiation responsive to an interaction with the emitted electromagnetic radiation. The method of the present disclosure may further comprise detecting electromagnetic radiation from the fluid, 114. The detected electromagnetic radiation can comprise the emitted electromagnetic radiation (changed or unchanged) and/or the secondary electromagnetic radiation from the fluid.

The emitted electromagnetic radiation can comprise the same or different wavelength as the detected electromagnetic radiation and/or secondary electromagnetic radiation. The emitted electromagnetic radiation and/or the detected electromagnetic radiation can comprise a single wavelength or a plurality of wavelengths.

The analyte content in the fluid can be determined based on the measured electromagnetic property. For example, a difference or similarity between the emitted electromagnetic radiation and detected radiation can be used to determine the analyte content. The detected electromagnetic radiation alone may be used to determine the analyte content.

In examples where the fluid comprises an electromagnetic property of absorption and/or transmittance, the measurement can be based on the difference or similarity in an intensity of the detected electromagnetic radiation relative to an intensity of the emitted electromagnetic radiation. For example, the fluid can absorb a portion of the emitted electromagnetic radiation as the emitted electromagnetic radiation passes through the fluid. A portion of the emitted electromagnetic radiation absorbed by the fluid can correspond to an absorbance measurement and the portion of the emitted electromagnetic radiation which passes (e.g., transmits) through the fluid can correspond to a transmittance measurement.

In examples where the fluid comprises an electromagnetic property of scattering, the measurement can be based on a change or similarity in an intensity of the detected electromagnetic radiation relative to an intensity of the emitted electromagnetic radiation. The fluid can scatter (e.g., deflect) at least a portion of the emitted electromagnetic radiation. A portion of the emitted electromagnetic radiation scattered by the fluid can correspond to a scattering measurement. The scattering can be in the form of Rayleigh scattering, Raman scattering, Mie scattering, dynamic light scattering, and combinations thereof. The scattering measurement can comprise a forward scattering value and a side scattering value which can be used to determine a particle size and a particle distribution.

In examples where the fluid comprises an electromagnetic property of photoluminescence, the measurement can be based on an intensity of the detected electromagnetic radiation. The detected electromagnetic radiation can comprise secondary electromagnetic radiation caused by photoluminescence of the fluid. For example, the emitted electromagnetic radiation can interact with (e.g., excite) the fluid and cause emission of secondary electromagnetic radiation by the fluid. The secondary electromagnetic radiation can be different than the emitted electromagnetic radiation.

In examples where the fluid comprises an electromagnetic property of reflectance, the measurement can be based on an intensity of the detected electromagnetic radiation relative to an intensity of the emitted electromagnetic radiation. For example, the fluid can reflect at least a portion of the emitted electromagnetic radiation. The at least a portion of the reflected electromagnetic radiation can be caused by the reflectance of the fluid. The reflected electromagnetic radiation can be diffuse, resulting in the emitted electromagnetic radiation taking multiple deflected paths, and/or specular, resulting in the emitted electromagnetic radiation taking a single deflected path.

The present disclosure further provides introducing a reagent to the fluid to facilitate determination of the analyte content. The reagent can be introduced to the fluid at any point in the method for determining the analyte content before measuring the electromagnetic property of the fluid. For example, the reagent can be introduced to the fluid before or after the fluid contacts the device. The reagent can be introduced to all of the fluid or a portion of the fluid. The reagent can comprise at least one of bicinchoninic acid (BCA) reagent, Coomassie reagent, ninhydrin reagent, ortho-phthalaldehyde (OPA) reagent, and fluorescamine reagent.

The reagent can affect the electromagnetic property of the fluid responsive to contact (e.g., interaction) with the analyte. The reagent can contact the analyte on a surface of the device or within the fluid. Contact of the reagent with the analyte can comprise a chemical interaction between the reagent and the analyte. The chemical interaction can comprise formation of ionic bonds, covalent bonds, or intermolecular forces, such as, electrostatic or van der Waals forces between the reagent and the analyte to form a reagent-analyte complex. For example, the fluid can have a first electromagnetic property with the reagent and the fluid can have a second electromagnetic property after the reagent contacts the analyte. Lower levels of analyte content in a fluid can be determined if a reagent is introduced to the fluid than if the analyte content is determined without introduction of the reagent.

For example, determining the analyte content in the fluid can comprise an assay, such as a colorimetric assay, a photoluminescence assay, and/or any assay suitable to determine the analyte content in a fluid. The assay can comprise at least one of a protein-copper chelation assay (e.g. a BCA reagent assay), a protein-dye binding assay (e.g. a Bradford assay using Coomassie reagent), a ninhydrin assay, and a primary amine labeling assay (e.g. an OPA reagent assay and/or a fluorescamine reagent assay).

The BCA assay can be used to determine an analyte content comprising protein. The BCA assay utilizes BCA reagent which can comprise bicinchoninic acid, sodium carbonate, sodium bicarbonate, sodium tartrate, and copper (II) sulfate pentahydrate at pH 11.25. The BCA reagent can be introduced to the fluid in order to detect protein within the fluid. The protein within the fluid can reduce the copper(II) ions to copper(I) ions. The copper(I) ions can be chelated by bicinchoninic acid to form a chelation complex. The absorption of the chelation complex can be measured at a wavelength in a range of 500 nm to 600 nm. For example, the absorption of the chelation complex can be measured at a wavelength of 562 nm.

The Bradford assay can be used to determine an analyte content comprising protein. The Bradford assay utilizes Bradford reagent which can comprise Coomassie Brilliant Blue G-250 dye, phosphoric acid, and an alcohol such as methanol or ethanol. The Bradford reagent can be introduced to the fluid in order to detect protein within the fluid. The protein within the fluid and the dye can chemically interact (e.g., bind noncovalently). The absorption of the dye-protein complex can be measured at a wavelength in a range of 550 nm to 655 nm. For example, the absorption of the dye-protein complex can be measured at a wavelength of 595 nm.

The ninhydrin (also called 2,2-dihydroxy-1H-indene-1,3 (2H)-dione) assay can be used to determine an analyte content comprising protein. The ninhydrin assay utilizes ninhydrin reagent which can comprise ninhydrin and hydrindantin in dimethyl sulfoxide (DMSO) and lithium acetate buffer at pH 5.2. The ninhydrin reagent can be introduced to the fluid in order to detect protein within the fluid based on the presence of primary amines which react with ninhydrin reagent to form a ninhydrin chromophore (also called Ruhemann's purple). The absorption of the ninhydrin chromophore can be measured at a wavelength in a range of 420 nm to 605 nm. For example, the absorption of the ninhydrin chromophore can be measured at 570 nm.

The OPA assay can be used to determine an analyte content comprising protein. The OPA assay utilizes OPA reagent which can comprise OPA, ethanol, 2-mercaptoethanol (also called 2-sulfanylethan-1-ol), and carbonate buffer at pH 10.5. The OPA reagent can be introduced to the fluid in order to detect protein within the fluid based on the presence of primary amines which react with OPA reagent to form a fluorescent product. Excitation of the fluorescent product (e.g., by the emitted electromagnetic radiation) can be performed at a wavelength in a range of 330 nm to 390 nm. For example, excitation of the fluorescent product can be performed at a wavelength of 340 nm. Detection of photoluminescence (e.g., detection of secondary electromagnetic radiation) of the fluorescent product can be performed at a wavelength in a range of 436 nm to 475 nm. For example, detection of photoluminescence of the fluorescent product can be performed at a wavelength of 455 nm.

The fluorescamine assay can be used to determine an analyte content comprising protein. The fluorescamine assay utilizes fluorescamine reagent which can comprise fluorescamine (also called 4'-phenylspiro[2-benzofuran-3,2'-furan]-1,3'-dione) dissolved in acetone. The fluorescamine reagent can be introduced to the fluid in order to detect protein within the fluid based on the presence of primary amines which react with fluorescamine reagent to form a fluorescent product. Excitation of the fluorescent product (e.g., by the emitted electromagnetic radiation) can be performed at a wavelength in a range of 370 nm to 420 nm. For example, excitation of the fluorescent product can be performed at a wavelength of 390 nm. Detection of photoluminescence by the fluorescent product can be performed at a wavelength in a range of 450 nm to 490 nm. For example, detection of photoluminescence by the fluorescent product can be performed at a wavelength of 460 nm, 465 nm, and/or 475 nm.

Determining the analyte content in the fluid can comprise multiple emitting, detecting, and/or measuring steps. For example, a first electromagnetic property of the fluid can be measured before the fluid contacts the device and a second electromagnetic property of the fluid can be measured after the fluid contacts the device. The first measurement can be compared to the second measurement to determine a similarity or a difference. Based on the comparison, the analyte content can be determined. The electromagnetic property of the fluid can be compared to a standard value and/or standard curve corresponding to a known analyte content value in order to determine the analyte content.

The present disclosure also provides, if necessary, adjusting a parameter of a treatment process for the device based on the analyte content, 116. The parameter can comprise at least one of a treatment temperature, a treatment time, a treatment pressure, a treatment agent concentration, a treatment agent type, a displayed message, and a cycle start/stop parameter. The parameter can be adjusted for all or part of the treatment process in any combination or variation desired by the operator.

For example, when the analyte content is at least a threshold value, a parameter can be adjusted (e.g., increased, decreased), and when the analyte content is less than the threshold value, a parameter can remain unchanged. In other examples, when the analyte content is at least a threshold value, a parameter can remain unchanged and when the analyte content is less than the threshold value, a parameter can be adjusted. Adjustment of a parameter can increase efficiency and/or effectiveness of the treatment process. For example, a treatment process can be completed in less time and/or with less wear on the device than an unadjusted treatment process. The parameter can be adjusted regardless of a threshold value (e.g., adjusted on a scale relative to the analyte content).

The treatment temperature can be adjusted to increase removal and/or elimination of debris and/or bioburden based on the analyte content. For example, increasing the treatment temperature can increase the amount of debris and/or bioburden that can be removed from the surface of the device (e.g., by increased solubility or increased treatment agent activity). The treatment temperature can be decreased to lower energy requirements for the treatment process.

The treatment time can be adjusted to increase removal of debris and bioburden based on the analyte content. For example, increasing the treatment time can increase the amount of debris and/or bioburden that is removed from the surface of the device. The treatment time can be decreased to remove debris and bioburden more efficiently.

The treatment agent concentration can be adjusted to increase removal of debris and bioburden. For example, increasing the treatment agent concentration can increase the effectiveness of the treatment agent and decreasing the treatment agent concentration can minimize costs, energy requirements, and/or residual waste.

A message can be adjusted and/or created. The message can comprise string (e.g., a sequence of characters) that may be hidden or displayed to an operator. For example, the message can comprise at least one of an instruction to adjust a treatment process parameter, an analyte content value, a location of an analyte content on the device, and a status of the treatment process.

A cycle start/stop parameter of the treatment process can be adjusted to skip (e.g., not perform) or repeat a portion of the treatment process. For example, a cycle start or stop time can be adjusted. A cycle of the treatment process can be a portion, stage, part, and/or sub-process in a treatment process.

Adjustment of a treatment process parameter can be executed automatically, based on the analyte content. Analyte content from a plurality of locations on the device can be determined, and the analyte contents from the plurality of locations can each be considered alone or in combination (e.g., averaged, weighted) when adjusting the treatment process. After the analyte content in the fluid is determined and, if necessary, a treatment process parameter is adjusted, the treatment process can be continued, 118. The determination of the analyte content can verify successful completion of a treatment process. For example, if the analyte content of the fluid is determined to be less than a threshold value, the treatment process could be verified as successfully completed. In other examples, if the analyte content of the fluid is determined to be at least a threshold value for a successfully treated device, the treatment process could be verified as successfully completed.

A threshold value for the analyte content can be, for example, a protein concentration, a carbohydrate concentration, a lipid concentration, a peptide concentration, a nucleic acid concentration, a polynucleotide concentration, a bacterium concentration, a virus concentration, a spore concentration, a eukaryote concentration, an archaeon concentration, a treatment agent concentration, a particle size, and a particle distribution. For example, if the protein concentration of the fluid is determined to be less than the threshold value, the treatment process could be determined to be successful. A threshold value can be at least 1.0 µg of protein per $cm^2$ such as, for example, at least 5.0 µg of protein per $cm^2$, at least 10 µg of protein per $cm^2$, at least 15 µg of protein per $cm^2$, at least 20 µg of protein per $cm^2$, at least 200 µg of protein per $cm^2$, at least 500 µg of protein per $cm^2$, or at least 750 µg of protein per $cm^2$. A threshold value can be 1000 µg or less of protein per $cm^2$ such as, for example, 5.0 µg or less of protein per $cm^2$, 10 µg or less of protein per $cm^2$, 15 µg or less of protein per $cm^2$, 20 µg or less of protein per $cm^2$, 50 µg or less of protein per $cm^2$, 250 µg or less of protein per $cm^2$, 500 µg or less of protein per $cm^2$, or 750 µg or less of protein per $cm^2$. A threshold value can range from 1.0 µg of protein per cm² to 1000 µg of protein per cm² such as, for example, 1.0 µg of protein per cm² to 20 µg of protein per cm², 1.0 µg of protein per cm² to 15 µg of protein per cm², 1.0 µg of protein per cm² to 10 µg of protein per cm², 5.0 µg of protein per cm² to 10 µg of protein per cm², 50 µg of protein per cm² to 750 µg of protein per cm², 200 µg of protein per cm² to 750 µg of protein per cm², or 200 µg of protein per cm² to 500 µg of protein per cm². A threshold value can be 6.4 µg of protein per cm².

Figure 2:
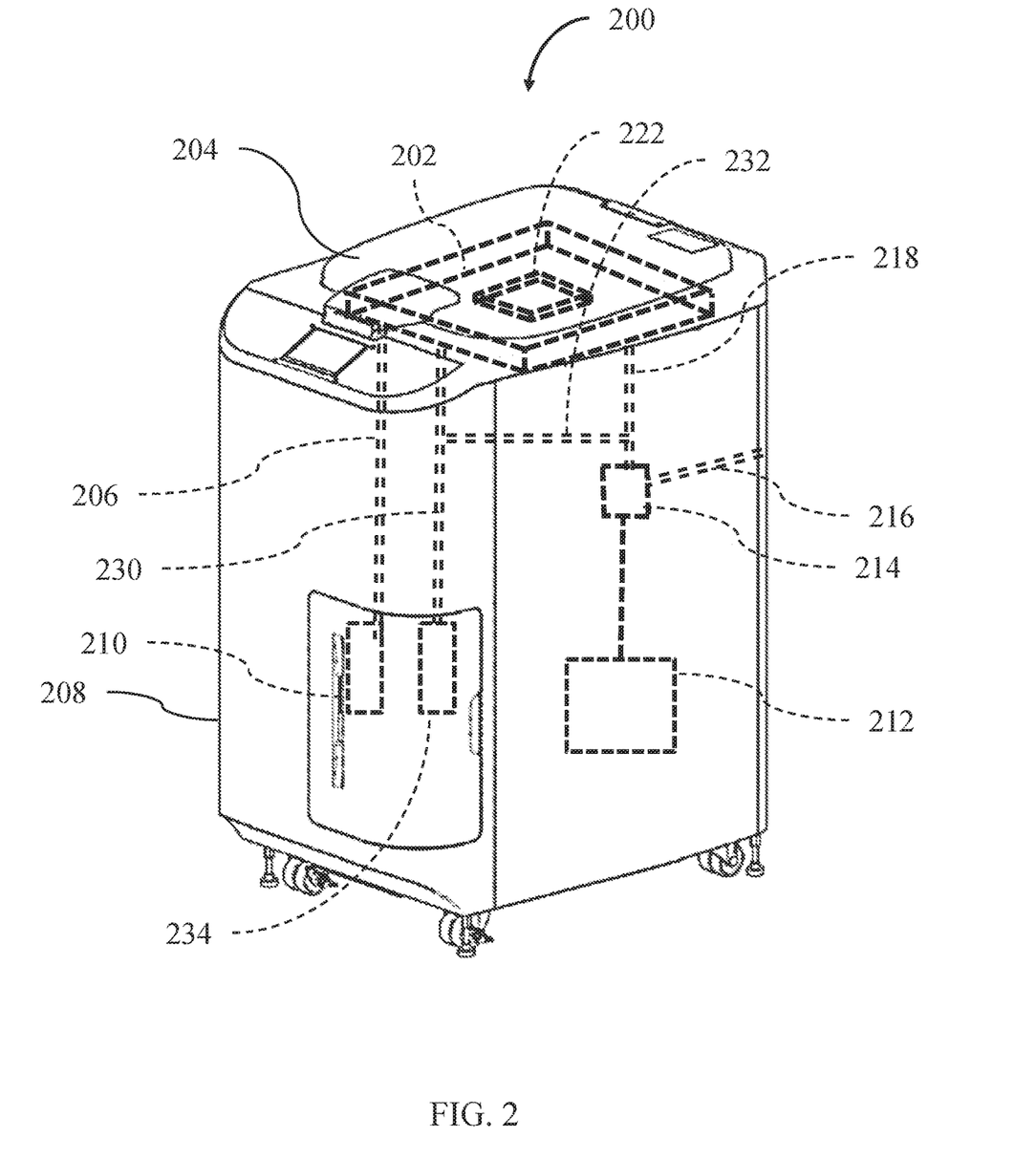
FIG. 2 is a perspective view of a non-limiting example of a system for determining an analyte content in fluid in a treatment apparatus according to the present disclosure.

Referring to FIG. 2, a system 200 for determining analyte content in a fluid within a treatment apparatus 208 is provided. The system 200 can comprise the treatment apparatus 208 and a detector 214 for determining the analyte content in the fluid. The treatment apparatus 208 can be, for example, an endoscope re-processor. The treatment apparatus 208 can comprise a basin 202, a lid 204, and a reservoir 210. The basin 202 can be configured to receive a device 222, such as a medical device, for treatment. For example, the basin 202 can comprise a volume and a shape suitable to receive the device 222. The basin 202 can be in fluid communication with the detector 214 and a drain line 216 via a fluid connection 218. The basin 202 can be configured to promote contact between a surface of the device 222 and the fluid. For example, a fluid dispenser (not shown in FIG. 2, discussed below) comprising at least one of a pump, a nozzle, a scrubbing apparatus, a tube, and a fitting can be disposed within the basin 202 and structured to dispense fluid onto a surface of the device 222. Fluid can be dispensed into contact with an outer and/or luminal surface of the device 222. The basin 202 can be configured in a manner that allows the device 222 to be submerged in the fluid, and arranged such that the fluid can flow fluid over a surface or through a lumen of the device 222.

The lid 204 can be positioned in a first configuration and a second configuration. The first configuration can enable access to the basin 202 for loading and/or unloading of a device 222. The second configuration can limit access to the basin 202 and can inhibit excess fluid from leaving the basin 202. For example, in the second configuration, the lid 204 may be positioned in a sealable arrangement with the basin 202 to inhibit access to the basin 202 while the device 222 is being treated with the fluid.

The reservoir 210 can be in fluid communication with the basin 202 and can provide fluid to the basin 202 via a fluid connection 206. The reservoir 210 can comprise at least one of water, a treatment agent, and a reagent. The basin 202 can be supplied with water via an external line (not shown in FIG. 2) that draws water from various suitable water sources. There may be a plurality of reservoirs 210 in fluid communication with the basin 202 and each reservoir can comprise at least one of water, a treatment agent, and a reagent.

The system 200 can comprise a second reservoir 234 for holding a reagent and introducing the reagent into the treatment process. The second reservoir 234 can be in fluid communication with the basin 202 via a fluid connection 230, and the second reservoir 234 can be in fluid communication with the detector 214 via a fluid connection 232. The second reservoir 234 and/or reservoir 210 can comprise an opaque material (e.g., to inhibit electromagnetic radiation from contacting and degrading the reagent) and can be temperature controlled (e.g., to inhibit temperature based degradation of the reagent). The second reservoir 234 can be configured to introduce reagent to the basin 202 and to the fluid connection 218. The second reservoir 234 can be configured to introduce reagent either to all of the fluid within the treatment apparatus 208 or a portion of the fluid within the treatment apparatus 208. The reservoir 234 can introduce reagent to the fluid before, after, and/or during the contacting of the surface of the device 222 with the fluid.

The detector 214 can be configured for electromagnetic communication with the treatment apparatus 208 and can measure an electromagnetic property of the fluid within the treatment apparatus 208. As used herein, the term "electromagnetic communication" means that electromagnetic radiation can travel between a first component and a second component with minimal, if any, degradation of the electromagnetic radiation. The detector 214 can emit electromagnetic radiation into fluid in the treatment apparatus 208 and the detector 214 can receive electromagnetic radiation from the fluid in the treatment apparatus 208. For example, the treatment apparatus 208 can comprise a port (e.g., tube, window, wall) which is at least partially transparent to electromagnetic radiation emitted by the detector 214 and the port can be positioned intermediate the detector 214 and the fluid within the treatment apparatus 208. The detector 214 can be positioned relative to the port in order to emit electromagnetic radiation into the port or receive electromagnetic radiation from the port. The detector 214 can be in direct contact with the fluid in the treatment apparatus 208.

The detector 214 can be in signal communication with a module 212. For example, the detector 214 can send signals (e.g., electrical impulses) which can be received by the module 212. The module 212 can send signals which can be received the detector 214. For example, the detector 214 can send signals to the module 212 via a wire or a wireless communication technology (e.g., Bluetooth). The module 212 can be configured to determine an analyte concentration and/or adjust a treatment process parameter based on the electromagnetic property measured by the detector 214.

A suitable detector can comprise a spectrophotometer, such as, for example, a microspectrophotometer available from CRAIC Technologies™, San Dimas, California, or a Thermo Scientific AquaMate 8000 UV-VIS Spectrophotometer (manufacturer model no. AQ8000) available from Thermo Fisher Scientific, Waltham, Massachusetts.

Figure 3:
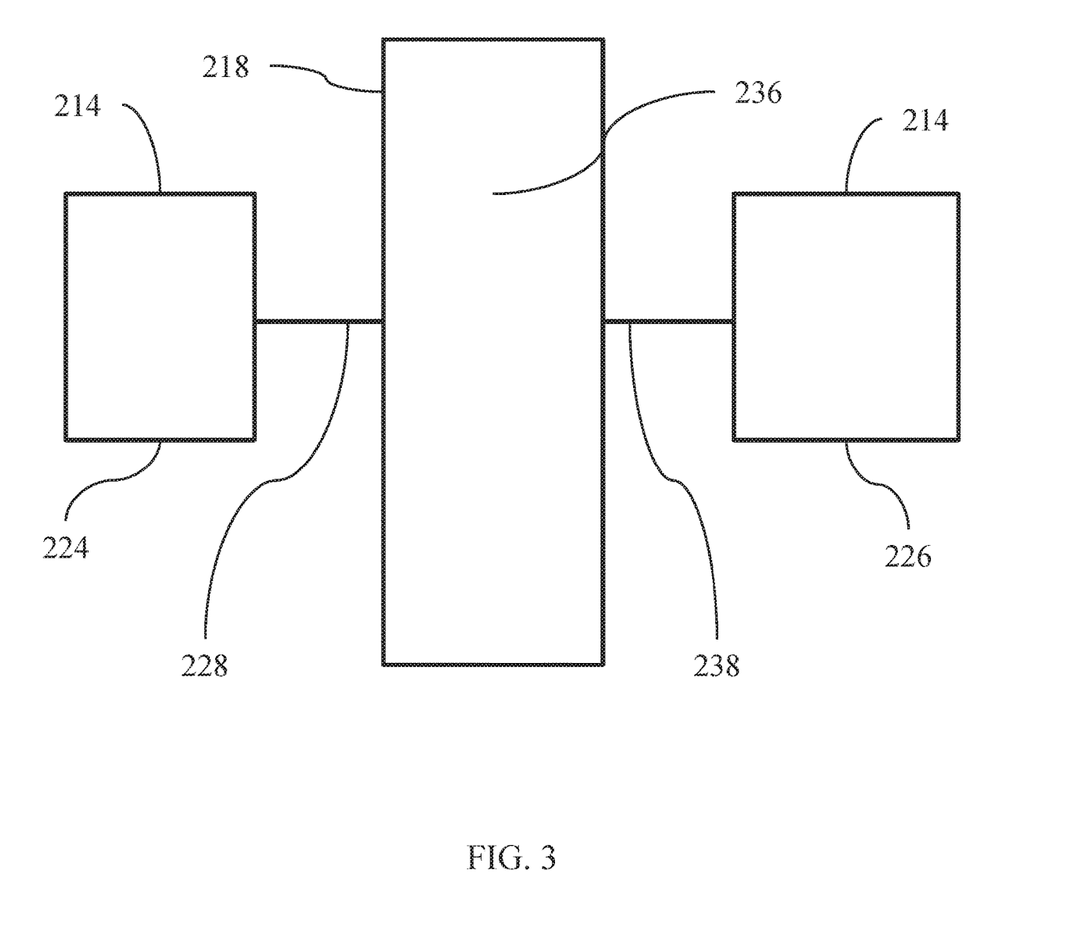
FIG. 3 is a schematic view of a non-limiting example of the detector for determining an analyte content in a fluid in a treatment apparatus according to the present disclosure.

FIG. 3 provides a schematic view of the detector 214 configuration of the present disclosure, wherein detector 214 is employed to determine analyte content in a fluid 236. As illustrated, the detector 214 can comprise an electromagnetic radiation source 224 and an electromagnetic radiation sensor 226. The electromagnetic radiation source 224 can be in electromagnetic communication with the fluid 236 and can be configured to emit electromagnetic radiation 228 into the fluid 236 in the treatment apparatus 208. The electromagnetic radiation source 224 can comprise any suitable radiation-emitting device, such as, for example, at least one of an incandescent bulb, a fluorescent bulb, a lamp, a light emitting diode, a laser diode, and a monochromator.

The electromagnetic radiation source 224 can be configured to emit electromagnetic radiation 228 comprising a same or a different wavelength as the electromagnetic radiation 238 detected by the electromagnetic radiation sensor 226. The electromagnetic radiation source 224 can be configured to emit electromagnetic radiation 228 comprising a single wavelength or a plurality of wavelengths.

The electromagnetic radiation source 224 can be configured to emit electromagnetic radiation 228 comprising a wavelength of at least 100 nm such as, for example, at least 190 nm, at least 330 nm, at least 370 nm, at least 420 nm, at least 500 nm, at least 550 nm, or at least 1 µm. The electromagnetic radiation source 224 can be configured to emit electromagnetic radiation 228 comprising a wavelength of 2 µm or less such as, for example, 1 µm or less, 700 nm or less, 655 nm or less, 605 nm or less, 600 nm or less, 420 nm or less, 390 nm or less, or 280 nm or less. The electromagnetic radiation source 224 can be configured to emit electromagnetic radiation 228 comprising a wavelength in a range from 100 nm to 2 µm such as, for example, 100 nm to 1 µm, 190 nm to 700 nm, 190 nm to 280 nm, 330 nm to 390 nm, 370 nm to 420 nm, 420 nm to 605 nm, 500 nm to 600 nm, or 550 nm to 655 nm. The electromagnetic radiation source 224 can be configured to emit electromagnetic radiation 228 comprising a wavelength of 190 nm, a wavelength of 205 nm, a wavelength of 280 nm, or any other wavelength suitable to measure an electromagnetic property of the fluid 236.

The electromagnetic radiation sensor 226 can be in electromagnetic communication with the fluid 236 and can be configured to detect electromagnetic radiation 238 from the fluid 236 in the treatment apparatus 208. The electromagnetic radiation sensor 226 can comprise a suitable radiation-detecting device, such as, for example, at least one of a photomultiplier, a photodiode, a silicon detector, and a charge-coupled device.

The electromagnetic radiation sensor 226 can be configured to detect electromagnetic radiation 238 comprising a same or different wavelength as the electromagnetic radiation 228 emitted by the electromagnetic radiation source 224. The electromagnetic radiation sensor 226 can be configured to detect electromagnetic radiation 238 comprising a single wavelength or a plurality of wavelengths.

The electromagnetic radiation sensor 226 can be configured to detect electromagnetic radiation 238 comprising a wavelength of at least 100 nm such as, for example, at least 190 nm, at least 420 nm, at least 436 nm, at least 450 nm, at least 500 nm, at least 550 nm, or at least 1 µm. The electromagnetic radiation sensor 226 can be configured to detect electromagnetic radiation 238 comprising a wavelength of 2 µm or less such as, for example, 1 µm or less, 700 nm or less, 655 nm or less, 605 nm or less, 600 nm or less, 490 nm or less, 475 nm or less, or 280 nm or less. The electromagnetic radiation sensor 226 can be configured to detect electromagnetic radiation 238 comprising a wavelength in a range from 100 nm to 2 µm such as, for example, 100 nm to 1 µm, 190 nm to 700 nm, 190 nm to 280 nm, 420 nm to 605 nm, 436 nm to 475 nm, 450 nm to 490 nm, 500 nm to 600 nm, or 550 nm to 655 nm. The electromagnetic radiation sensor 226 can be configured to detect electromagnetic radiation 238 comprising a wavelength of 190 nm, a wavelength of 205 nm, a wavelength of 280 nm, or any other wavelength suitable to measure an electromagnetic property of the fluid 236.

Figure 4:
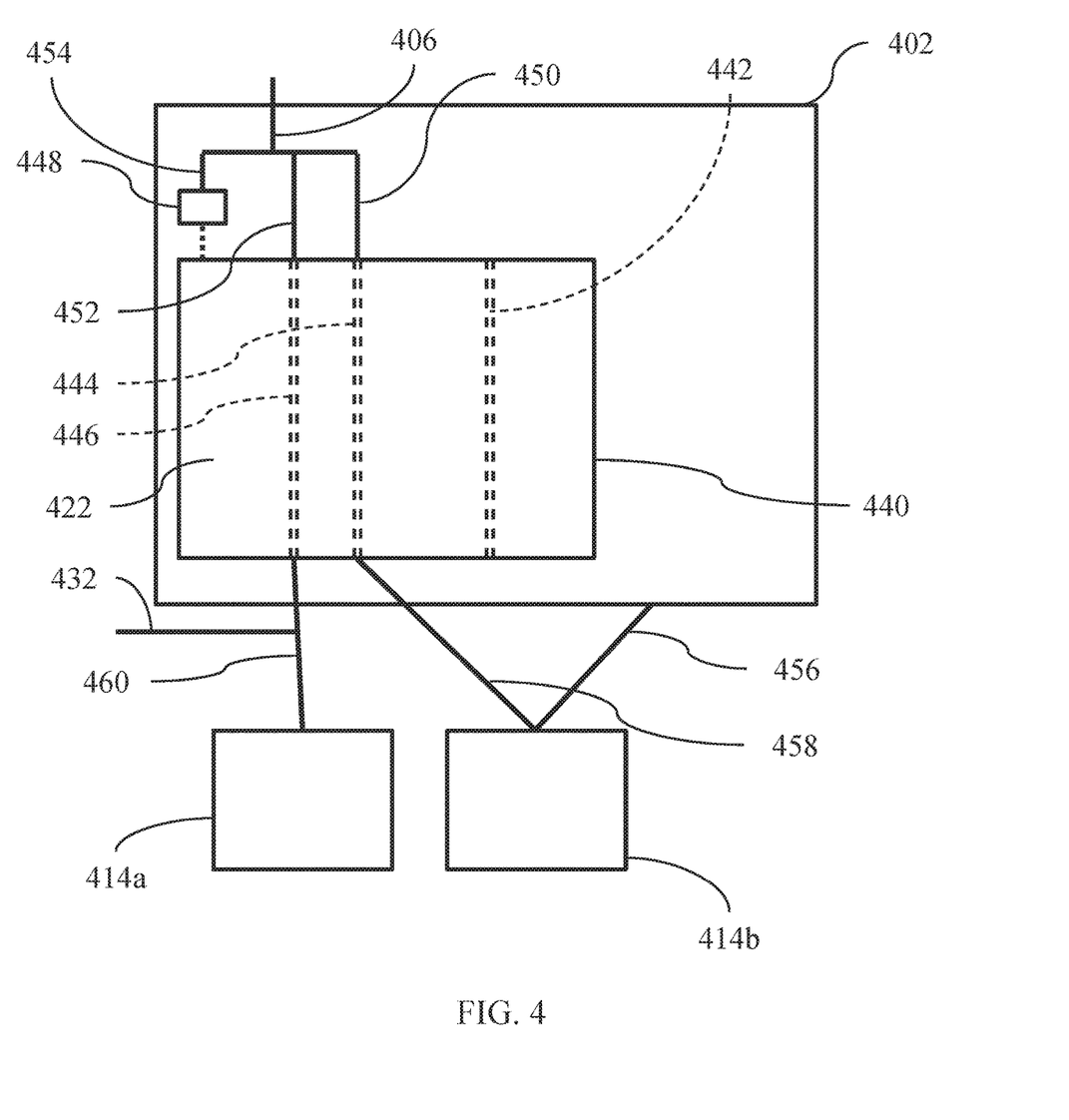
FIG. 4 is a schematic view of a non-limiting example of a system for determining an analyte content in a fluid in a treatment apparatus according to the present disclosure.

FIG. 4 illustrates a schematic front view of a system for determining an analyte content in a fluid in a treatment apparatus according to the present disclosure. As illustrated, a device 422 can be positioned within the basin 402 of a treatment apparatus (e.g., treatment apparatus 208). The device 422 can comprise a first lumen 442, a second lumen 444, and a third lumen 446. The device 422 can comprise a surface, such as, for example, an outer surface 440, a luminal surface of the first lumen 442, a luminal surface of the second lumen 444, and a luminal surface of the third lumen 446.

Fluid source 406 can receive fluid from a reservoir (e.g., reservoir 210, second reservoir 234), the basin 402 (e.g., basin 402 via recirculation), and/or fluid input (e.g., external line). The fluid source 406 can distribute the fluid to the fluid connections 450, 452, 454. Alternatively, the fluid connections 450, 452, 454 can have separate fluid sources or more than one fluid source (not shown in FIG. 4).

A fluid dispenser 448 can receive fluid from the fluid source 406 via fluid connection 454 and can introduce fluid to the outer surface 440 of the device 422. For example, the fluid dispenser 448 can be configured to spray the outer surface 440 of the device 422 with the fluid and/or flow the fluid over the outer surface 440 of the device 422. The device 422 can be submerged in fluid in the basin 402 to contact the outer surface 440 with fluid. Regardless of the form of by which fluid is introduced to the outer surface 440, the fluid can contact the outer surface 440, dissolve and/or suspend analyte on the outer surface 440, if any, and flow into the basin 402. The fluid dispenser 448 can comprise at least one of a spray arm, a spray nozzle, a fitting, and a tube.

In examples comprising submerging the device 422 in fluid, an exposed lumen of the device 422, such as, the first lumen 442 of the device 422 can receive fluid from the basin 402. A fluid connection (not shown) can be connected to and provide fluid to the first lumen 442. Regardless of the fluid input to the luminal surface of the first lumen 442, the fluid can contact the luminal surface within the first lumen 442, dissolve and/or suspend analyte on the luminal surface of the first lumen 442, if any, and flow into the basin 402.

The analyte dissolved and/or suspended from the luminal surface of the first lumen 442 and/or the outer surface 440 can be determined by the detector 414b via fluid connection 456 by measuring the fluid property of the fluid received from the basin 402. The fluid property of the fluid within the basin 402 can be affected by analyte on a single surface (e.g., only the outer surface 440, only a luminal surface) or a plurality of surfaces (e.g., the outer surface 440 and a luminal surface, two or more luminal surfaces).

The second lumen 444 can receive fluid from the fluid connection 450 and the third lumen 446 can receive fluid from the fluid connection 452. The fluid received by the second lumen 444 can contact the luminal surface within the second lumen 444, dissolve and/or suspend analyte on the luminal surface of the second lumen 444, if any, and flow into the detector 414b via fluid connection 458. The analyte dissolved and/or suspended from the luminal surface of the second lumen 444 can be determined by the detector 414b by measuring the fluid property of the fluid received from the second lumen 444.

The fluid received by the third lumen 446 can contact the luminal surface within the third lumen 446, dissolve and/or suspend analyte on the luminal surface of the third lumen 446, if any, and flow into the detector 414a via fluid connection 460. The analyte dissolved and/or suspended from the luminal surface of the third lumen 446 can be determined by the detector 414a by measuring the fluid property of the fluid received from the third lumen 446.

Fluid can be introduced into fluid connection 460 by fluid line 432 prior to the fluid from the third lumen 446 entering the detector 414a. For example, the fluid line 432 can provide reagent to the fluid connection 460. The fluid line 432 can provide regent to the fluid connection 456 and 458, if desired (not shown).

As illustrated in FIG. 4, fluid can contact a luminal surface within lumens 444, 446 and can be directly introduced to detectors 414a 414b, while bypassing the basin 402. One of detectors 414a, 414b can receive fluid from two or more of lumens 442, 444, 446 at the same time or from each lumen 442, 444, 446 at separate times permitting distinct measurements. The fluid from two or more of lumens 442, 444, 446 or from a lumen 442, 444, 446 and the basin 402 can be mixed prior to entering the detector 414a or 414b to permit a single measurement of a combined fluid. Detectors 414a, 414b can each receive fluid from the same lumens 442, 444, 446 or different lumens 442, 444, 446. Detectors 414a, 414b can receive fluid from only the basin 402 or a combination of a lumen 442, 444, 446 and the basin 402. The quantity and arrangement of detectors 414a, 414b is for illustration purposed only should not be considered limiting.

Various aspects of the present disclosure include, but are not limited to, the aspects listed in the following numbered clauses.

1. A method for determining an analyte content in a fluid, comprising: positioning a device for treatment in a treatment apparatus; contacting a surface of the device with the fluid; and determining the analyte content in the fluid based on an electromagnetic property of the fluid following the contacting the surface of the device with the fluid. The determining comprising: measuring the electromagnetic property of the fluid. The measuring comprises: emitting electromagnetic radiation into the fluid in the treatment apparatus; and detecting electromagnetic radiation from the fluid.
2. The method of clause 1, wherein the electromagnetic property comprises at least one of absorbance, transmittance, scattering, photoluminescence, and reflectance.
3. The method of any one of clauses 1-2, wherein the analyte content is at least one of a concentration, a particle size, and a particle distribution.
4. The method of any one of clauses 1-3, further comprising introducing a reagent to the fluid, wherein the reagent comprises an electromagnetic property responsive to contact with analyte.
5. The method of any one of clauses 1-4, further comprising adjusting a parameter of a treatment process for the device based on the analyte content, wherein the parameter comprises at least one of a treatment temperature, a treatment time, a treatment pressure, a treatment agent concentration, a treatment agent type, a message, and a cycle start/stop parameter.
6. The method of any one of clauses 1-5, wherein the surface of the device comprises analyte and wherein contacting the surface of the device in the treatment apparatus with the fluid comprises transferring at least a portion of the analyte from the device to the fluid.
7. The method of clause 5, wherein the analyte comprises at least one of a protein, a carbohydrate, a lipid, a peptide, a nucleic acid, a polynucleotide, a bacterium, a virus, a spore, a eukaryote, an archaeon, and a treatment agent.
8. The method of any one of clauses 1-7, wherein the device is a medical device.
9. The method of any one of clauses 1-8, wherein contacting the surface of the device in the treatment apparatus with the fluid comprises contacting a luminal surface of the endoscope with the fluid.
10. The method of any one of clauses 1-9, wherein the fluid comprises at least one of water and a treatment agent.
11. A system for determining an analyte content in a fluid, comprising: a treatment apparatus; a detector for determining the analyte content in the fluid in the treatment apparatus, the detector configured for electromagnetic communication with the treatment apparatus. The detector comprising: an electromagnetic radiation source configured to emit electromagnetic radiation into the fluid in the treatment apparatus; an electromagnetic radiation sensor configured to detect electromagnetic radiation from the fluid; and the detector configured to measure an electromagnetic property of the fluid based on detected electromagnetic radiation from the fluid to determine the analyte content in the fluid.
12. The system of clause 11, wherein the electromagnetic property comprises at least one of absorbance, transmittance, scattering, photoluminescence, and reflectance.
13. The system of any one of clauses 11-12, wherein the electromagnetic radiation source is suitable to emit electromagnetic radiation at a wavelength in a range of 100 nm to 2 µm and the electromagnetic radiation sensor is suitable to detect electromagnetic radiation at a wavelength in a range of 100 nm to 2 µm.
14. The system of any one of clauses 11-13, wherein the electromagnetic radiation source is suitable to emit electromagnetic radiation at a wavelength in a range of 190 nm to 700 nm and the electromagnetic radiation sensor is suitable to detect electromagnetic radiation at a wavelength in a range of 190 nm to 700 nm.
15. The system of any one of clauses 11-14, further comprising a module configured to adjust a treatment process parameter of the treatment apparatus based on the analyte content in the fluid, wherein the parameter comprises at least one of a treatment temperature, a treatment time, a treatment pressure, a treatment agent concentration, a treatment agent type, a displayed message, and a cycle start/stop parameter.
16. The system of any one of clauses 11-15, wherein the treatment apparatus is configured to receive a device, and the device is a medical device.
17. The system of clause 16, wherein the treatment apparatus further comprises a first fluid connection and a second fluid connection, the first fluid connection is in fluid communication with a first lumen of the medical device and suitable to introduce the fluid to the first lumen, the second fluid connection is in fluid communication with the first lumen and suitable to receive the fluid from the first lumen, wherein the detector is in electromagnetic communication with the second fluid connection and suitable to measure an electromagnetic property of the fluid from the second fluid connection.
18. The system of clause 17, wherein the treatment apparatus further comprises a third fluid connection and a fourth fluid connection, the third fluid connection is in fluid communication with a second lumen of the medical device and suitable to introduce the fluid to the second lumen, the fourth fluid connection is in fluid communication with the second lumen and suitable to receive the fluid from the second lumen, and a second detector in electromagnetic communication with the fourth fluid connection, the second detector suitable for measuring an electromagnetic property of the fluid from the fourth fluid connection.
19. The system of any one of clauses 11-18, wherein the treatment apparatus comprises an endoscope re-processor.
20. The system of any one of clauses 11-19, wherein the fluid comprises at least one of water and a treatment agent.
21. The system of any one of clauses 11-20, wherein the surface of the device comprises analyte.
22. The system of any one of clauses 11-21, wherein the analyte comprises at least one of a protein, a carbohydrate, a lipid, a peptide, a nucleic acid, a polynucleotide, a bacterium, a virus, a spore, a eukaryote, an archaeon, and a treatment agent.

23. The system of any one of clauses 11-22, wherein the fluid comprises at least one of water and a treatment agent.
24. The system of any one of clauses 11-23, wherein the electromagnetic radiation source comprises at least one of an incandescent bulb, a fluorescent bulb, a light emitting diode, and a laser diode.
25. The system of any one of clauses 11-24, wherein the electromagnetic radiation sensor comprises at least one of a photomultiplier, a photodiode, and a silicon detector.
26. A system for determining the protein content in a fluid, comprising: an endoscope re-processor comprising a pathway in fluid communication with a surface of an endoscope, the surface of the device comprising protein; a detector for determining the protein content in the fluid in the endoscope re-processor, the detector configured for electromagnetic communication with the endoscope re-processor. The detector comprising: an electromagnetic radiation source configured to emit electromagnetic radiation at a wavelength in a range of 190 nm to 700 nm into the fluid in the endoscope re-processor; and an electromagnetic radiation sensor configured to detect electromagnetic radiation at a wavelength in a range of 190 nm to 700 nm from the fluid, the detector configured to measure an electromagnetic property of the fluid based on the detecting to determine the protein content in the fluid.
27. The method of clause 8, wherein the medical device is an endoscope.
28. The system of clause 16, wherein the medical device is an endoscope.

One skilled in the art will recognize that the herein described components (e.g., operations), devices, objects, and the discussion accompanying them are used as examples for the sake of conceptual clarity and that various configuration modifications are contemplated. Consequently, as used herein, the specific exemplars set forth and the accompanying discussion are intended to be representative of their more general classes. In general, use of any specific exemplar is intended to be representative of its class, and the non-inclusion of specific components (e.g., operations), devices, and objects should not be taken limiting.

With respect to the appended claims, those skilled in the art will appreciate that recited operations therein may generally be performed in any order. Also, although various operational flows are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

One skilled in the art will recognize that the herein described components, devices, operations/actions, and objects, and the discussion accompanying them, are used as examples for the sake of conceptual clarity and that various configuration modifications are contemplated. Consequently, as used herein, the specific examples/embodiments set forth and the accompanying discussion are intended to be representative of their more general classes. In general, use of any specific exemplar is intended to be representative of its class, and the non-inclusion of specific components, devices, operations/actions, and objects should not be taken limiting. While the present disclosure provides descriptions of various specific aspects for the purpose of illustrating various aspects of the present disclosure and/or its potential applications, it is understood that variations and modifications will occur to those skilled in the art. Accordingly, the invention or inventions described herein should be understood to be at least as broad as they are claimed and not as more narrowly defined by particular illustrative aspects provided herein.

What is claimed is:

1. A method for determining an analyte content in a fluid, comprising:
    positioning a device for treatment in a treatment apparatus;
    contacting a surface of the device with the fluid;
    determining the analyte content in the fluid based on an electromagnetic property of the fluid following the contacting the surface of the device with the fluid, the determining comprising:
    measuring the electromagnetic property of the fluid, the measuring comprising:
    emitting electromagnetic radiation into the fluid in the treatment apparatus; and detecting electromagnetic radiation from the fluid;
    adjusting a parameter of a treatment process for the device based on the analyte content, wherein the parameter is a treatment agent type and;
    continuing the treatment process.

2. The method of claim 1, wherein the electromagnetic property comprises at least one of absorbance, transmittance, scattering, photoluminescence, and reflectance.

3. The method of claim 1, wherein the analyte content is at least one of a concentration, a particle size, and a particle distribution.

4. The method of claim 1, further comprising introducing a reagent to the fluid, wherein the reagent comprises an electromagnetic property responsive to contact with analyte.

5. The method of claim 1, wherein the analyte comprises at least one of a protein, a carbohydrate, a lipid, a peptide, a nucleic acid, a polynucleotide, a bacterium, a virus, a spore, a eukaryote, an archaean, and a treatment agent.

6. The method of claim 1, wherein the surface of the device comprises analyte and wherein contacting the surface of the device in the treatment apparatus with the fluid comprises transferring at least a portion of the analyte from the device to the fluid.

7. The method of claim 1, wherein the device is a medical device.

8. The method of claim 7, wherein the medical device is an endoscope.

9. The method of claim 1, wherein contacting the surface of the device in the treatment apparatus with the fluid comprises contacting a luminal surface of an endoscope with the fluid.

10. The method of claim 1, wherein the fluid comprises at least one of water and a treatment agent.

11. A system for determining an analyte content, comprising:
    a treatment apparatus;
    first and second detectors for determining the analyte content in a fluid in the treatment apparatus, the first detector fluidly connected to a first location and the second detector fluidly connected to a second location, each detector configured for electromagnetic communication with the treatment apparatus, each detector comprising:

an electromagnetic radiation source configured to emit electromagnetic radiation into the fluid in the treatment apparatus;

an electromagnetic radiation sensor configured to detect electromagnetic radiation from the fluid;

each detector configured to measure an electromagnetic property of the fluid based on detected electromagnetic radiation from the fluid to determine the analyte content in the fluid; and a module configured to adjust a treatment process parameter of the treatment apparatus based on the analyte content in the fluid, wherein the parameter is a treatment agent type.

12. The system of claim 11, wherein the electromagnetic property comprises at least one of absorbance, transmittance, scattering, photoluminescence, and reflectance.

13. The system of claim 11, wherein the electromagnetic radiation source is suitable to emit electromagnetic radiation at a wavelength in a range of 100 nm to 2 llm and the electromagnetic radiation sensor is suitable to detect electromagnetic radiation at a wavelength in a range of 100 nm to 2 llm.

14. The system of claim 11, wherein the electromagnetic radiation source is suitable to emit electromagnetic radiation at a wavelength in a range of 190 nm to 700 nm and the electromagnetic radiation sensor is suitable to detect electromagnetic radiation at a wavelength in a range of 190 nm to 700 nm.

15. The system of claim 11, wherein the treatment apparatus is configured to receive a device, and the device is a medical device.

16. The system of claim 15, wherein the medical device is an endoscope.

17. The system of claim 15, wherein the treatment apparatus further comprises a first fluid connection and a second fluid connection, the first fluid connection is in fluid communication with a first lumen of the medical device and suitable to introduce the fluid to the first lumen, the second fluid connection is in fluid communication with the first lumen and suitable to receive the fluid from the first lumen, wherein the first detector is in electromagnetic communication with the second fluid connection and suitable to measure an electromagnetic property of the fluid from the second fluid connection.

18. The system of claim 17, wherein the treatment apparatus further comprises a third fluid connection and a fourth fluid connection, the third fluid connection is in fluid communication with a second lumen of the medical device and suitable to introduce the fluid to the second lumen, the fourth fluid connection is in fluid communication with the second lumen and suitable to receive the fluid from the second lumen, wherein the second detector is in electromagnetic communication with the fourth fluid connection, the second detector suitable for measuring an electromagnetic property of the fluid from the fourth fluid connection.

19. The system of claim 11, wherein the treatment apparatus comprises an endoscope re-processor.

20. The system of claim 11, wherein the fluid comprises at least one of water and a treatment agent.

21. The system of claim 11, wherein the surface of the device comprises analyte.

22. The system of claim 11, wherein the analyte comprises at least one of a protein, a carbohydrate, a lipid, a peptide, a nucleic acid, a polynucleotide, a bacterium, a virus, a spore, a eukaryote, an archaean, and a treatment agent.

23. The system of claim 11, wherein the electromagnetic radiation sensor comprises at least one of a photomultiplier, a photodiode, and a silicon detector.

24. The system of claim 11, wherein the electromagnetic radiation source comprises at least one of an incandescent bulb, a fluorescent bulb, a light emitting diode, and a laser diode.

25. A system for determining the protein content in a fluid, comprising:

an endoscope re-processor comprising a sprayer for spraying the fluid over a surface of an endoscope, the surface of the device comprising protein;

a detector for determining the protein content in the fluid in the endoscope re-processor, the detector configured for electromagnetic communication with the endoscope re-processor, the detector comprising:

an electromagnetic radiation source configured to emit electromagnetic radiation at a wavelength in a range of 190 nm to 700 nm into the fluid in the endoscope re-processor; and an electromagnetic radiation sensor configured to detect electromagnetic radiation at a wavelength in a range of 190 nm to 700 nm from the fluid, the detector configured to measure an electromagnetic property of the fluid based on the detecting to determine the protein content in the fluid; and a module configured to adjust a treatment process parameter of the treatment apparatus based on the protein content in the fluid, wherein the parameter is a treatment agent type.

* * * * *